United States Patent [19]

Eckhardt et al.

[11] Patent Number: 4,831,166

[45] Date of Patent: May 16, 1989

[54] PREPARATION OF ALPHA-SUBSTITUTED UPSILON-BUTYROLACTONES

[75] Inventors: Heinz Eckhardt, Ludwigshafen; Walter Gramlich, Edingen-Neckarhausen; Walter Best, Weisenheim; Klaus Halbritter, Mannheim, all of Fed. Rep. of Germany

[73] Assignee: BASF Aktiengesellschaft, Ludwigshafen, Fed. Rep. of Germany

[21] Appl. No.: 47,131

[22] Filed: May 8, 1987

[30] Foreign Application Priority Data

May 22, 1986 [DE] Fed. Rep. of Germany ....... 3617177

[51] Int. Cl.$^4$ ................. C07D 307/14; C07D 307/12; C07D 307/06
[52] U.S. Cl. .................... 549/323; 549/326; 549/321; 549/324
[58] Field of Search ............... 549/295, 326, 323, 321, 549/324

[56] References Cited

U.S. PATENT DOCUMENTS 3,299,100 1/1967 Phillips ............................ 549/326
4,276,218 6/1981 Lantzsch ........................... 549/215

OTHER PUBLICATIONS

Yufit et al, "Reactions of Carbonyl, etc" CA98 : 142689d (1983).
Fedorynski et al, "Esters and Nitriles, etc" CA92 : 41373s (1980).
Chelintsev et al, "The Condensation, etc" CA32 : 2099 (1937).
Adams et al, "Condensation of Acetoacetic, etc" JACS 72 (1980) 4368.
Russell et al, "The Malanic Ester, etc" JACS 69 (1947) 11.
*Compt. Rend.*, 234 (1952) pp. 1293 and 1694.
*Beilstein* III/IV pp. 4229, 4244, and 4252.
Houben-Weyl, *Methoden der organ. chm.*, p. 662.
Henkel-Referate 20 (1984) pp. 61–66.

*Primary Examiner*—Richard L. Raymond
*Assistant Examiner*—Patricia L. Morris
*Attorney, Agent, or Firm*—Oblon, Fisher, Spivak, McClelland & Maier

[57] ABSTRACT

γ-butyrolactones of the general formula I

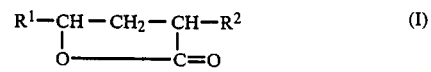

where $R^1$ is hydrogen or alkyl of 1 to 4 carbon atoms which may be substituted by lower alkoxy or acyloxy and $R^2$ is hydrogen or straight-chain or branched alkyl which is unsubstituted or substituted by a functional group or is aryl, are prepared by reacting an alkylene oxide of the general formula II

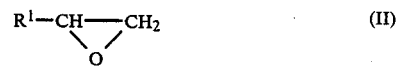

with an acylacetate of the general formla III

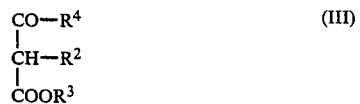

where $R^1$ and $R^2$ have the above meanings and $R^3$ and $R^4$ are each alkyl of 1 to 6 carbon atoms or aryl, and $R^4$ may furthermore be hydrogen, in the presence of a catalyst at elevated temperatures, by a process in which the reaction is carried out in the presence of an alkali metal halide, of an ammonium halide, preferably a quaternary ammonium halide, of a phosphonium halide, of an alkali metal phosphate or of an alkali metal carbonate at from 20° to 200° C. and under from 1 to 50 bar.

16 Claims, No Drawings

PREPARATION OF ALPHA-SUBSTITUTED UPSILON-BUTYROLACTONES

The present invention relates to an improved process for the preparation of γ-butyrolactones by reacting alkyl acylacetates with alkylene oxides in the presence of catalysts.

Some γ-butyrolactones are interesting scents and others are useful intermediates for the synthesis of a large number of heterocyclic compounds, such as the pyrrolidones and pyrrolidines.

The commonest method for the preparation of γ-butyrolactones is that due to Rothstein (cf. Compt. Rend. 234 (1952), 1293 and 1694), in which appropriately substituted malonates are first converted to the alkali metal salt which is then reacted with an alkylene oxide to give a γ-butyrolactone which contains an additional ester group, which finally has to be hydrolyzed and decarboxylated. From the present day point of view, this process has several decisive disadvantages. On the one hand, there is very substantial pollution of the waste-water by the salts produced from the bases and acids used in stoichiometric amounts. On the other hand, the necessity of several reaction steps, some of which take place in an alkaline medium and others in an acidic medium, makes the process engineering very expensive. Other disadvantages of the process are the corrosion problems encountered, the relatively large amount of byproducts formed and the high price of malonates. In spite of the stated substantial disadvantages, this process is the standard method for the preparation of γ-butyrolactones )cf. Beilstein, Supplements III/IV, vol. 17/5, eg. pages 4229, 4244 and 4252).

The preparation of γ-butyrolactones by reacting alkyl acylacetates with alkylene oxides in the presence of catalysts has in principle also long been known. For example, according to Houben-Weyl, Methoden der organischen Chemie, 4th edition, vol. 6/2, page 662, 4-hydroxy-2-methylbutyrolactone (α-methyl-γ-butyrolactone) is obtained in a yield of 50% when ethylene oxide acts on sodium ethyl α-methylacetate in alcohol.

Although the reaction of ethyl α-methyl acetate with ethylene oxide in the presence of anhydrous potassium acetate in a closed tube gives yields of 70%, this reaction is an exception and is not possible with higher alkylacetates.

In addition to the unsatisfactory yields, a particularly great disadvantage of this process is the stoichiometric use of a base, and attempts have therefore been made to find novel catalysts, of which catalytic amounts are sufficient.

It was found that, with catalytic amounts of sodium methylate, no reaction of α-alkylacetates with ethylene oxide takes place, but that a superbase, eg. tetrabutylammonium hexachloroantimonate, gives a reaction product which, after secondary reactions with an alkali and an acid, finally gives a corresponding lactone. Yields for this reaction were not stated (cf. Henkel-Referate 20 (1984), 61–66, especially 65–66).

It is an object of the present invention to improve the process for the preparation of γ-butyrolactones by reaction of alkyl acylacetates with alkylene oxides so that, on the one hand, it is universally applicable and, on the other hand, it can be carried out using small amounts of a catalyst which is very simple to obtain.

We have found that this object is achieved, and that the reaction of acetoacetates with alkylene oxides takes place with yields of 90% of theory or higher, if ionic halides are used as catalysts. This discovery is surprising since halide ions are considered to be very weak bases, and the literature results indicate that either particularly strong bases or salts with complex anions are preferable. Furthermore, the use of the tetrabutylammonium cation cannot be critical for the success of the reaction, since alkali metal halides give just as good results as quaternary ammonium halides.

The present invention accordingly relates to a process for the preparation of γ-butyrolactones of the general formula I

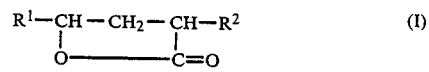

where $R^1$ is hydrogen or alkyl of 1 to 4 carbon atoms which may be substituted by lower alkoxy or acyloxy, preferably acetoxy, and $R^2$ is straight-chain or branched alkyl of 1 to 12, preferably 1 to 4, carbon atoms which is unsubstituted or substituted by functional groups such as lower alkoxy, acyloxy, amido, hydroxyl, aryl or halogen, or is aryl, in particular phenyl, by reacting an alkylene oxide of the general formula II

with an acylacetate of the general formula III

where $R^1$ has the above meanings, $R^3$ and $R^4$ are each branched or straight-chain alkyl of 1 to 6, preferably 1 or 2, carbon atoms or aryl, preferably phenyl, $R^4$ may additionally be hydrogen and $R^5$ is hydrogen or one of the radicals stated for $R^2$, in the presence of a catalyst at elevated temperatures, wherein the reaction is carried out in the presence of from 0.001 to 0.1 mole of an alkali metal halide, of an ammonium halide, preferably a quaternary ammonium halide, of a phosphonium halide, of an alkali metal phosphate or of an alkali metal carbonate per mole of acylacetate at from 20° to 200° C., preferably from 60° to 150° C., and under from 1 to 50, preferably from 1 to 20, bar.

Suitable catalysts are alkali metal halides, such as LiCl, NaCl, KCl, KF, KBr, NaI, LiF, NaBr and KI. Another group of suitable catalysts comprises ammonium halides and phosphonium halides, preferably quaternary ammonium or phosphonium halides, and, in the case of the preferred ammonium cations, either all four substituents are lower alkyl radicals of 1 to 6 carbon atoms or one or more of the four radicals are benzyl or a fairly long alkyl group of 6 to 20 carbon atoms. Examples are tetramethylammonium chloride, tetraethylammonium bromide, tetrabutylammonium chloride, benzyltrimethylammonium bromide and methyltrialkylammonium chlorides which are sold under the names Adogen 464 from Schering AG or Aliquat ® 336 from General Mills Inc., USA. Examples of preferred quaternary phosphonium halides are triphenylmethylphosphonium chloride, triphenylethylphosphonium chloride, tributylmethylphosphonium bromide, trimethoxymethylphosphonium bromide and triethoxymethylphosphonium bromide. Of the halide anions, the fluoride, chloride, bromide and iodide are preferably used. However, it is also possible to use other anions referred to as pseudohalides, eg. cyanide, azide, isocyanate and thiocyanate, and phosphate and carbonate, of which the phosphates or carbonates may also become industrially important.

Examples of preferred alkylene oxides of the general formula II are ethylene oxide, propylene oxide, butylene oxide, acetoxyethylene oxide, methoxyethylene oxide and ethoxyethylene oxide.

Examples of suitable acylacetates of the general formula III are unsubstituted acylacetates and acylacetates which are substituted in the α-position, the type of alcohol used for the esterification being unimportant for carrying out the reaction. Usually, esters of the lower alcohols, ie. alcohols of not more than 6 carbon atoms, in particular esters of methanol or ethanol, are used.

$R^5$ in the acetoacetates substituted in the α-position may be alkali or aryl, which itself may be substituted by other functional groups, such as lower alkoxy, lower acyloxy, amido, hydroxyl, aryl or halogen.

Preferred radicals $R^5$ are methyl, ethyl, propyl, isopropyl, butyl, isobutyl, sec-butyl, amyl, isoamyl, 2-methylbutyl hexyl, 2-ethylbutyl, 2-ethylhexyl, cyclohexyl, heptyl, 2-propylpentyl, octyl, nonyl, decyl, phenyl, benzyl, 2-hydroxyethyl, 2-hydroxypropyl, 2-hydroxybutyl, carbomethoxymethyl and carbomethoxyethyl.

$R^4$ in III can in principle be varied as widely as radical $R^5$. However, since it does not appear in the end product I of the reaction, it is advantageous to provide readily obtainable substituents in this position. These are, for example, phenyl, ethyl, propyl and in particular methyl.

The reaction of acetoacetates substituted in the α-position is simply a matter of the radical $R^5$ of the acylacetate reappearing in the α-position of the γ-butyrolactone of the formula I, ie. $R^2$ being identical to $R^5$. If, on the other hand, acylacetates which are unsubstituted in the α-position are used (ie. $R^5$ is H), in general both activated α-hydrogen atoms undergo a reaction with the alkylene oxide of the formula II. This applies in particular to the activated lower alkylene oxides, such as ethylene oxide ($R^1$ is H) and propylene oxide ($R^1$ is $CH_3$). Hence, in the reaction of, in each case, 2 moles of a lower alkylene oxide with 1 mole of an acetoacetate of the formula III which is unsubstituted in the α-position, γ-butyrolactones of the general formula I, where $R^2$ is 2-hydroxyalkyl or 2-acetoxyalkyl, are formed as a result of subsequent intramolecular rearrangement reactions. The formation of these γ-butyrolactones can be represented by the following equation:

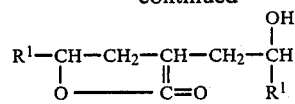

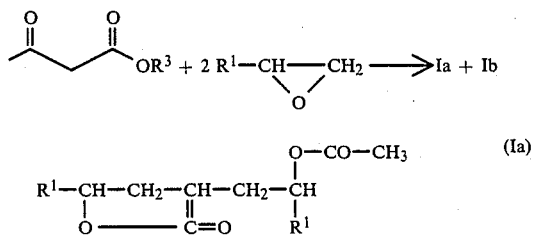

In general, mixtures of the γ-butyrolactones of the formulae Ia and Ib (where $R^1$ is H, $CH_3$ or $C_2H_5$) are formed in this reaction. However, by varying the reaction conditions, Ia or Ib can be preferentially formed. For example, the use of a small amount of solvent preferentially gives the α-(2-acetoxyalkyl) compound, whereas a larger amount of solvent preferentially results in the α-(2-hydroxyalkyl) compound. Conversion to Ib can be completed by treatment with small amounts of an alkali metal alcoholate.

The most advantageous reaction conditions for each desired γ-butyrolactone can be determined by simple preliminary experiments.

The present invention therefore furthermore relates to a process, as described in detail above, for the preparation of γ-butyrolactones of the general formula I where $R^1$ is hydrogen and $R^2$ is 2-hydroxyethyl or 2-acetoxyethyl, wherein in each case from 1 to 3 moles of ethylene oxide are reacted with 1 mole of an acetoacetate of the general formula III where $R^5$ is hydrogen and $R^3$ has the meanings stated in claim 1, and to a process for the preparation of γ-butyrolactone of the general formula I where $R^1$ is methyl and $R^2$ is 2-hydroxyprop-1-yl or 2-acetoxyprop-1-yl, wherein in each case from 1 to 3 moles of propylene oxide are reacted with 1 mole of an acetoacetate of the general formula III where $R^5$ is hydrogen and $R^3$ has the meanings stated in claim 1.

The reactions are preferably carried out in a lower alcohol as the solvent; the solvent and the alcohol component of the ester group in the acylacetate III do not have to be identical in order to obtain a good result in the reaction. Preferred solvents are methanol, ethanol, propanol, isopropanol, butanol and tert-butanol.

The reactions are carried out at from room temperature to 200° C., preferably from 60° to 150° C., and advantageously under superatmospheric pressure of from 1 to 50, preferably from 1 to 20, bar. The reaction times are from 5 to 20, preferably from 8 to 15, hours.

In a preferred embodiment, the solvent, the catalyst and the acylacetate III are initially taken, and the alkylene oxide II is metered in at the reaction temperature in the course of from 1 to 10 hours. However, it is also possible for the alkylene oxide II to be initially taken, in addition, from the beginning of the reaction. After a subsequent reaction time which is such that the abovementioned total reaction time is maintained, the reaction product can be isolated in a conventional manner (filtration, extraction, distillation etc.).

The starting materials III and II can be used in a stoichiometric ratio, or one of the components can be used in excess. Advantageous ratios are from 0.5 to 3, preferably from 0.8 to 1.5, moles of alkylene oxide II per mole of acetoacetate III, where equimolar stoichiometry is not present. The solvent is used in an amount of from 0 to 500%. The amount of catalyst used is from 0.001 to 0.1, preferably from 0.003 to 0.05, mole per mole of III.

To obtain a particularly pure product, particularly where α-alkylacetoacetates of the formula III having fairly long α-alkyl radicals, such as ethyl α-hexylacetoacetate, it may be advantageous to treat the reaction mixture, after the reaction according to the invention, with a small amount of a strong base in order to complete the formation of I (starting from starting compounds III where $R^5$ is not H) or the formation of Ib (starting from starting compounds III where $R^5$ is H). This base must then be neutralized again by treatment with a mineral acid. In this way, these butyrolactones too are obtained in yields greater than 90% and in excellent purity.

Suitable strong bases for this purpose are alkali metal hydroxides, alkali metal alcoholates and tertiary amines, in particular $NaOCH_3$.

The amount used is in general from 0.1 to 0.5 mole per mole of III. Suitable mineral acids are hydrochloric acid, sulfuric acid, phosphoric acid and nitric acid.

With the aid of the novel process, the γ-butyrolactones of the general formula I, which are desirable scents or intermediates for the synthesis of heterocycles, can be prepared in a simple and cheap manner, without causing serious wastewater problems and in very good yields, by reacting the acylacetates III with the alkylene oxides II.

The Examples which follow illustrate the process.

EXAMPLES 1 TO 8

A mixture consisting of the α-alkylacetoacetates of the formula III as stated in the Table below, in the amount stated there, and the same amount by weight of the stated solvent, in each case 1.5% by weight, based on III used, of tetramethylammonim chloride and the amount of ethylene oxide stated there was heated at 100° C. for 12 hours in a 300 ml autoclave. Distillation of the reacted mixtures gave the yields of the corresponding α-alkylbutyrolactone of the formula I which is stated in the Table.

in a 20 l autoclave. 2.11 kg (52.8 moles) of ethylene oxide were metered in at 100° C. in the course of 4 hours, after which the pressure was increased to 20 bar with nitrogen and the reaction mixture was allowed to react for a further 10 hours at 100° C.

In order to obtain a particularly pure product, 500 g (9.26 moles) of sodium methylate in the form of a 30% strength solution in methanol were then added to the reacted mixture under atmospheric pressure and heating was continued for a further 4 hours at 65° C. to complete the formation of I. Thereafter, the reaction mixture was evaporated down, and treated with 3 l of 2N sulfuric acid for 3 hours at 100° C. The organic phase was worked up by distillation to give 6.33 kg of 99.9% pure 3-hexylbutyrolactone. The yield was 93% of theory.

EXAMPLE 10

A mixture of 107 g of ethyl α-hexylacetoacetate, 107 g of ethanol, 34 g of propylene oxide and 1.5 g of tetramethylammonium chloride was heated in an autoclave for 10 hours at 120° C. The reacted mixture was heated with 5 g of sodium ethylate for a further 5 hours at 65° C. and then distilled. 84.6 g of 3-hexyl-5-methylbutyrolactone were obtained. The yield was 92% of theory.

EXAMPLE 11

A mixture of 58 g of methyl acetoacetate, 44 g of ethylene oxide, 3 g of NaCl and 70 ml of methanol was heated in an autoclave under autogenous pressure for 12 hours at 80° C. Thereafter, the methanol was distilled off, the residue was taken up with water, and the solution was washed with a little chloroform and distilled. 52.6 g of 2-(2-hydroxyethyl)-γ-butyrolactone were obtained, corresponding to a yield of 81% of theory.

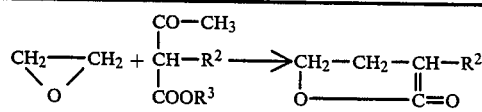

| Ex-ample | Alkyl acetoacetate III $R^2$ | $R^3$ | Amount [g] | Solvent | Ethylene oxide II Amount [g] | Yield of I [g] | [%] |
|---|---|---|---|---|---|---|---|
| 1 | —$CH_3$ | —$CH_3$ | 78 | methanol | 31.7 | 55.2 | 92 |
| 2 | —$C_2H_5$ | —$C_3H_7$ | 120 | propanol | 37.0 | 69.4 | 87 |
| 3 | —$C_4H_9$ | —$C_2H_5$ | 86 | ethanol | 22.0 | 59.7 | 91 |
| 4 | —$CH_2$—$CH(CH_3)$—$CH_2$—$CH_3$ | —$C_2H_5$ | 89 | ethanol | 23.5 | 61.1 | 88 |
| 5 | —$C_6H_{13}$ | —$C_2H_5$ | 64 | ethanol | 15.8 | 47.4 | 93 |
| 6 | —$C_6H_{13}$ | —$CH_3$ | 100 | methanol | 26.4 | 76.5 | 90 |
| 7 | —$CH_2$—$CH(C_2H_5)$—$CH_2$—$CH_3$ | —$C_2H_5$ | 64 | ethanol | 15.8 | 46.4 | 91 |
| 8 | (t-butyl-phenyl)—$CH_2$— | —$C_2H_5$ | 100 | ethanol | 19.1 | 75.2 | 90 |

EXAMPLE 9

A mixture consisting of 8.56 kg (40 moles) of ethyl α-hexylacetoacetate, 0.95 kg of methanol and 80 g (0.38 mole) of triethylbenzylammonium chloride was heated 9.3 g (corresponding to 8% of theory) of 2-(2-hydroxyethyl)-γ-butyrolactone were also obtained in the chloroform used for washing, which it was possible to work up.

EXAMPLE 12

The procedure described in Example 11 was followed, except that 10 g of $K_2CO_3$ were used instead of 3 g of NaCl. 54 g of 2-(2-hydroxyethyl)-γ-butyrolactone were obtained, corresponding to a yield of 83% of theory.

EXAMPLE 13

The procedure described in Example 11 was followed, except that 10 g of $Na_3PO_4.12H_2O$ were used instead of 3 g of NaCl. 21.7 g (corresponding to a 34% yield) of 2-(2-hydroxyethyl)-γ-butyrolactone and 50.7 g (corresponding to a 59% yield) of 2-(2-acetoxyethyl)-γ-butyrolactone of boiling point 100°–105° C./0.3 mbar were obtained.

EXAMPLE 14

58 g (0.5 mole) of methyl acetoacetate, 44 g of ethylene oxide, 3 g of NaCl and 30 g of methanol were heated in an autoclave under autogenous pressure for 12 hours at 80° C. Thereafter, the methanol was distilled off, the residue was taken up in chloroform, and the solution was washed with a little water and distilled. 65.3 g of α-(2-acetoxyethyl)-γ-butyrolactone of boiling point 100°–105° C./0.3 bar were obtained, corresponding to a yield of 76% of theory. The aqueous phase also contained 8.5 g of α-(2-hydroxyethyl)-γ-butyrolactone, corresponding to 13% of theory.

We claim:

1. A process for the preparation of an α-substituted γ-butyrolactone of the formula I:

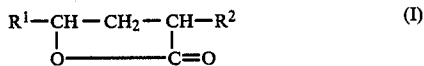

wherein $R^1$ is hydrogen or an alkyl group of 1 to 4 carbon atoms which is unsubstituted or substituted by lower alkoxy or acyloxy groups; and $R^2$ is a straight-chain or branched-chain alkyl group of 1 to 12 carbon atoms which is unsubstituted or substituted by lower alkoxy, acyloxy, amido, hydroxyl, phenyl, t-butylphenyl or halogen groups, or $R^2$ is a phenyl group; by reacting an alkylene oxide of the formula II:

with an acyl acetate of the formula III:

wherein $R^1$ is as defined above; $R^3$ and $R^4$ are each branched- or straight-chain alkyl groups of 1 to 6 carbon atoms or phenyl; or $R^4$ is hydrogen; and $R^5$ is hydrogen or a radical as defined for $R^2$; in the presence of a catalyst at elevated temperatures, wherein the reaction is carried out in the presence of from 0.001 to 0.1 mole of an alkali metal halide, an ammonium halide, a phosphonium halide, an alkali metal phosphate or an alkali metal carbonate per mole of acyl acetate at from 20° to 200° C. and under a pressure of from 1 to 50 bar.

2. A process for the preparation of a γ-butyrolactone of the formula I as claimed in claim 1, wherein the reaction is carried out at from 60° to 150° C.

3. The process for the preparation of a γ-butyrolactone of the formula I as claimed in claim 1, wherein the reaction is carried out at a pressure of under from 1 to 20 bar.

4. The process for the preparation of a γ-butyrolactone of the formula I as claimed in claim 1, having α-alkyl radicals of 6 or more carbons wherein the reaction mixture is further treated for 1–10 hours at from 20° to 150° C. with from 0.02 to 0.5 mole of a strong base, which is then neutralized with a mineral acid.

5. The process as claimed in claim 1 for the preparation of a γ-butyrolactone of the formula I where $R^1$ is hydrogen and $R^2$ is 2-hydroxyethyl or 2-acetoxyethyl, wherein from 1 to 3 moles of ethylene oxide are reacted with 1 mole of an acetoacetate of the formula III where $R^5$ is hydrogen and $R^3$ has the meanings stated in claim 1.

6. The process as claimed in claim 1 for the preparation of a γ-butyrolactone of the formula I where $R^1$ is methyl and $R^2$ is 2-hydroxyprop-1-yl or 2-acetoxyprop-1-yl, wherein from 1 to 3 moles of propylene oxide are reacted with 1 mole of an acetoacetate of the formula III where $R^5$ is hydrogen and $R^3$ has the meanings stated in claim 1.

7. The process as claimed in claim 1, for the preparation of a γ-butyrolactone of the formula I, wherein the reaction is carried out in the presence of a quaternary ammonium halide.

8. The process as claimed in claim 1, wherein said alkali metal halide is selected from the group consisting of LiCl, NaCl, KCl, KF, KBr, NaI, LiF, NaBr and KI.

9. The process as claimed in claim 7, wherein said quaternary ammonium halide has four alkyl substituents of 1 to 6 carbon atoms, or one or more of said alkyl substituents having an alkyl group of 6 to 20 carbon atoms.

10. The process as claimed in claim 7, wherein said quaternary ammonium halide is selected from the group consisting of tetramethyl ammonium chloride, tetraethyl ammonium bromide, tetrabutyl ammonium chloride, and benzyltrimethylammonium bromide.

11. The process as claimed in claim 1, wherein said phosphonium halide is a quaternary phosphonium halide selected from the group consisting of triphenylmethylphosphonium chloride, triphenylethylphosphonium chloride, tributylmethylphosphonium chloride, trimethoxymethylphosphonium bromide and triethoxymethylphosphonium bromide.

12. The process as claimed in claim 1, wherein said alkylene oxide is selected from the group consisting of ethylene oxide, propylene oxide, butylene oxide, acetoxyethylene oxide, methoxyethylene oxide and ethoxyethylene oxide.

13. The process as claimed in claim 1, which is carried out in the presence of a lower alkyl alcohol as a solvent.

14. The process as claimed in claim 1, wherein from about 0.5 to 3 moles of alkylene oxide are used per mole of acyl acetate.

15. The process as claimed in claim 1, wherein the catalyst is used in an amount of from 0.003 to 0.05 mole per mole of acyl acetate.

16. The process as claimed in claim 4, wherein said strong base is an alkali metal hydroxide, alkali metal alcoholate and tertiary amine.

* * * * *